United States Patent [19]

Hess et al.

[11] Patent Number: 4,849,218

[45] Date of Patent: Jul. 18, 1989

[54] ORAL GARLIC PREPARATIONS AND PROCESS FOR PREPARING SAME

[75] Inventors: Anton H. Hess, Hirschhorn; Siegfried Mehn, Eberbach-Igelsbach; Holger Schönmann, Eberbach, all of Fed. Rep. of Germany

[73] Assignee: R. P. Scherer GmbH, Baden, Fed. Rep. of Germany

[21] Appl. No.: 929,350

[22] Filed: Nov. 12, 1986

[30] Foreign Application Priority Data

Nov. 22, 1985 [DE] Fed. Rep. of Germany ....... 3541304

[51] Int. Cl.⁴ .............................................. A01N 63/02
[52] U.S. Cl. .................................. 424/94.1; 424/406; 424/408; 424/472; 424/474
[58] Field of Search .......................... 426/49, 52, 638; 424/406, 472, 408, 474, 94.1

[56] References Cited

U.S. PATENT DOCUMENTS

| 2,618,561 | 11/1952 | Spinka et al. | 426/49 |
| 2,760,869 | 8/1956 | Yanick | 426/49 |
| 4,547,375 | 10/1985 | Mersfelder et al. | 426/52 |
| 4,649,052 | 3/1987 | Sumi et al. | 426/49 |

FOREIGN PATENT DOCUMENTS

| 0180672 | 5/1986 | European Pat. Off. | |
| 052248 | 8/1973 | Japan | 426/638 |
| 004241 | 7/1975 | Japan | 426/638 |
| 0094049 | 8/1978 | Japan | 426/49 |
| 0113051 | 10/1978 | Japan | 426/52 |
| 0018563 | 2/1981 | Japan | 426/52 |
| 0034151 | 2/1985 | Japan | 426/638 |
| 8303061 | 9/1983 | World Int. Prop. O. | |

Primary Examiner—Ellis P. Robinson
Assistant Examiner—P. J. Ryan
Attorney, Agent, or Firm—Wegner & Bretschneider

[57] ABSTRACT

Oral garlic preparations contain garlic powder as well as the enzyme allinase, in which each of the components is spatially separated from the other and are recombined only after having been orally administered.

2 Claims, No Drawings

ORAL GARLIC PREPARATIONS AND PROCESS FOR PREPARING SAME

The present invention relates to oral garlic preparations which contain garlic powder as well as the enzyme allinase.

BACKGROUND OF THE INVENTION

The oral garlic preparations are known to either contain only garlic powder which has proven to be nearly ineffective, or they contain garlic powder as well as the enzyme allinase. Garlic powder is either a drug which has been ground or a dried drug extract in which the naturally occurring enzyme allinase has been destroyed. The destruction of the enzyme is usually effected by heating at a temperature above 70° C. for a short period of time at which temperature of the other ingredients of garlic remain virtually unchanged or by chemical methods.

Preparations containing garlic powder together with the enzyme allinase are unstable and have the known unpleasant odour of garlic. Further preparations which contain varying residual amounts of the enzyme allinase are subject to variations in stability, activity and odour trouble. It has not been possible to make oral garlic preparations which meet all of the requirements for such a preparation.

SUMMARY OF THE INVENTION

It is the object of the present invention to develop oral garlic preparations which contain the garlic powder in an active form and the enzyme allinase, which are readily prepared, and have storage stability, do not cause annoying bad odour and exhibit the full activity of garlic when administered.

According to the present invention, these objectives can be attained by having both of the components spatially separated from one another but recombined upon oral administration.

For example, said objectives can be attained by separately microencapsulating each of the two components and having both types of microcapsules present in a mixture with one another. Furthermore, it is possible to convert the enzyme into the form of spray-solidified pellets, the fat base of which has a melting point of below 40° C., and to convert the garlic powder into the form of spray-solidified pellets and to mix the two kinds of pellets with one another. When mixing these two kinds of pellets it may be desirable to admix small amounts of corn starch which reduces the tackiness of the pellets. This mixture may then be filled into hard gelatin capsules in a known manner.

Another method of attaining said objectives consists of providing the garlic powder and the enzyme in a form suitable for making tablets therefrom and then compressing these two pre-mixes in a known manner to give a two-layer tablet.

Finally, it is possible to suspend the two components in a mixture of saturated triglycerides and vegetable oil and to fill the resulting suspension into soft gelatin capsules in a known manner.

All of the preparations formed in the above manner have proven to be stable and permit the two components to react with each other after administration and to develop the active ingredients of the natural garlic.

Thus, the subject matter of the present invention comprises the oral preparation forms as described above and the process for preparing same.

Further details, typical embodiments of the oral preparations and of the processes for preparing same are illustrated in further detail in the following examples.

EXAMPLE 1

Fat Pellets in Hard Capsules 20 kg of garlic powder are dispersed in 80 kg of melted glycerol monostearate to give a fine dispersion. The hot suspension is pelletized by spray-solidification through a rotating nozzle having a 0.5 mm bore. 5 kg of allinase (powder) are also pelletized by spray-solidification in 20 kg of melted hard fat the temperature of which must not exceed 40° C. Upon sifting off the fractions having suitable grain sizes the two kinds of pellets are mixed in a cone impeller together with 0.25 % corn starch. The final pellet mixture is filled into hard capsules in an amount of 501.25 mg per capsule.

EXAMPLE 2

Two-Layer Film Tablet 20 kg of garlic powder are dispersed in a melt comprising 35.8 kg of cetyl alcohol and 1.7 kg of lecithin. The cooled suspension is coarsely pulverized in a suitable manner. The powder is admixed with 1.5 kg of corn starch and 1 kg of pyrogenic silica (Aerosil 200 ®) (Powder 1).

Granules are prepared from 5 kg of allinase (powder), 13 kg of hardened castor oil, 5 kg of corn starch, 1 kg of stearic acid and 1 kg of methylcellulose by dry mixing (Powder 2).

In a two-layer tablet press, tablet cores are prepared from 240 mg of powder (1) and 100 mg of powder (2). The cores are pre-coated with a moisture-repellent shellac film and then coated with suspension of Pharmacoat 606 ®, titanium dioxide, PEG 6000 with Iron Oxide Yellow in water.

EXAMPLE 3

Soft Gelatin Capsules 20 kg of allinase (powder) and 80 kg of garlic powder are suspended in a mixture of 54 kg saturated triglycerides and 146 kg of vegetable oil. The suspension is homogenized in a suitable manner, sifted and de-aerated. Each of the soft gelatin capsules is filled in a known manner with 300 mg of the suspension.

We claim:

1. A storage stable, oral garlic preparation comprising:
   an active garlic powder;
   the enzyme allinase;
   the two components being spatially separated from one another so as to prevent them from reacting with one another prior to their oral administration, upon which administration they are recombined;
   the preparation being in a form selected from the group consisting of:
   a preparation comprising a mixture of microcapsules in which each of the components has been separately encapsulated;
   a preparation comprising a mixture of pellets in which the enzyme is present in the form of spray-solidified pellets having a fat base which has a melting point of less than 40° C. and the garlic powder is present in the form of spray-solidified pellets;

a preparation comprising a two-layer tablet in which the garlic powder and the enzyme are present in separate layers; and a preparation comprising a soft gelatine capsule containing a mixture of saturated triglycerides and vegetable oil in which the garlic powder and the enzyme are suspended.

2. A preparation according to claim 1, wherein the preparation is in the form of a mixture of pellets, the mixture being filled into hard gelatine capsules.

* * * * *